US011529197B2

(12) United States Patent
Kronman

(10) Patent No.: US 11,529,197 B2
(45) Date of Patent: Dec. 20, 2022

(54) DEVICE AND METHOD FOR TRACKING THE POSITION OF AN ENDOSCOPE WITHIN A PATIENT'S BODY

(71) Applicant: EndoChoice, Inc., Alpharetta, GA (US)

(72) Inventor: Achia Kronman, Pardes Hana (IL)

(73) Assignee: EndoChoice, Inc., Alpharetta, GA (US)

( * ) Notice: Subject to any disclaimer, the term of this patent is extended or adjusted under 35 U.S.C. 154(b) by 0 days.

(21) Appl. No.: 16/656,000

(22) Filed: Oct. 17, 2019

(65) Prior Publication Data
US 2020/0046437 A1    Feb. 13, 2020

Related U.S. Application Data

(63) Continuation of application No. 15/335,249, filed on Oct. 26, 2016, now abandoned.
(Continued)

(51) Int. Cl.
*A61B 1/00* (2006.01)
*A61B 34/20* (2016.01)
(Continued)

(52) U.S. Cl.
CPC .......... *A61B 34/20* (2016.02); *A61B 1/00006* (2013.01); *A61B 1/00066* (2013.01); *A61B 5/062* (2013.01); *A61B 5/066* (2013.01); *A61B 5/068* (2013.01); *A61B 5/7253* (2013.01); *A61B 90/361* (2016.02); *A61B 90/98* (2016.02); *A61B 2034/2048* (2016.02); *A61B 2034/2051* (2016.02); *A61B 2034/2055* (2016.02);
(Continued)

(58) Field of Classification Search
None
See application file for complete search history.

(56) References Cited

U.S. PATENT DOCUMENTS 3,639,714 A   2/1972  Fujimoto
3,955,064 A   5/1976  Demetrio
(Continued)

FOREIGN PATENT DOCUMENTS

CA    2297986    3/1999
CA    2765559    12/2010
(Continued)

OTHER PUBLICATIONS

Notice of Allowance dated Apr. 12, 2017 for U.S. Appl. No. 14/603,137.
(Continued)

*Primary Examiner* — Timothy J Neal
(74) *Attorney, Agent, or Firm* — Bookoff McAndrews, PLLC

(57) ABSTRACT

Systems and methods of tracking the position of an endoscope within a patient's body during an endoscopic procedure is disclosed. The devices and methods include determining a position of the endoscope within the patient in the endoscope's coordinate system, capturing in an image fiducial markers attached to the endoscope by an external optical tracker, transforming the captured fiducial markers from the endoscope's coordinate system to the optical tracker's coordinate system, projecting a virtual image of the endoscope on a model of the patient's organ, and projecting or displaying the combined image.

20 Claims, 7 Drawing Sheets

Related U.S. Application Data

(60) Provisional application No. 62/247,232, filed on Oct. 28, 2015.

(51) Int. Cl.

| | | |
|---|---|---|
| *A61B 90/00* | (2016.01) | |
| *A61B 90/98* | (2016.01) | |
| *A61B 5/06* | (2006.01) | |
| *A61B 5/00* | (2006.01) | |
| *A61M 25/00* | (2006.01) | |

(52) U.S. Cl.
CPC .............. *A61B 2034/2057* (2016.02); *A61B 2034/2059* (2016.02); *A61B 2090/062* (2016.02); *A61B 2090/365* (2016.02); *A61B 2090/366* (2016.02); *A61B 2090/367* (2016.02); *A61B 2090/3945* (2016.02); *A61B 2090/3979* (2016.02); *A61B 2090/3983* (2016.02); *A61B 2560/0223* (2013.01); *A61M 2025/0008* (2013.01)

(56) References Cited

U.S. PATENT DOCUMENTS

| | | |
|---|---|---|
| 4,027,697 A | 6/1977 | Bonney |
| 4,037,588 A | 7/1977 | Heckele |
| 4,084,401 A | 4/1978 | Belardi |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | McKenna |
| 5,547,467 A | 8/1996 | Tsuyuki |
| 5,571,114 A * | 11/1996 | Devanaboyina ... A61B 1/00151 606/1 |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,651,043 A | 7/1997 | Tsuyuki |
| 5,662,588 A | 9/1997 | Iida |
| 5,674,182 A | 10/1997 | Suzuki |
| 5,676,673 A | 10/1997 | Ferre |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | McKenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,860,913 A | 1/1999 | Yamaya |
| 5,870,234 A | 2/1999 | EbbesmeierneeSchitthof |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 | 8/2001 | Yoon |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | Mayer, III |
| 6,712,760 B2 | 3/2004 | Sano |
| 6,832,984 B2 | 12/2004 | Stelzer |
| 6,888,119 B2 | 5/2005 | Iizuka |
| 6,895,268 B1 | 5/2005 | Rahn et al. |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,504,136 B1 * | 8/2013 | Sun .................. A61B 5/1076 600/407 |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |

(56) References Cited

U.S. PATENT DOCUMENTS

| | | |
|---|---|---|
| 2001/0036322 A1 | 11/2001 | Bloomfield |
| 2002/0017515 A1 | 2/2002 | Obata |
| 2002/0047897 A1 | 4/2002 | Sugimoto |
| 2002/0077533 A1 | 6/2002 | Bieger et al. |
| 2002/0077543 A1 | 6/2002 | Grzeszczuk |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0138556 A1* | 7/2004 | Cosman ............... A61B 90/10 600/424 |
| 2004/0158129 A1 | 8/2004 | Okada |
| 2004/0160682 A1 | 8/2004 | Miyano |
| 2004/0176663 A1 | 9/2004 | Whitin |
| 2004/0176683 A1 | 9/2004 | Whitin et al. |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Broach |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0149129 A1 | 7/2006 | Watts |
| 2006/0169845 A1 | 8/2006 | Maahs |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0162095 A1 | 1/2007 | Kimmel |
| 2007/0049803 A1 | 3/2007 | Moriyama |
| 2007/0055100 A1 | 3/2007 | Kato |
| 2007/0055128 A1 | 3/2007 | Glossop |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | DeLorme |
| 2007/0213591 A1 | 9/2007 | Aizenfeld |
| 2007/0225553 A1 | 9/2007 | Shahidi |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0249932 A1* | 10/2007 | Shahinian ............ A61B 1/00193 600/421 |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045274 A1 | 2/2008 | Yasushi |
| 2008/0058601 A1 | 3/2008 | Fujimori |
| 2008/0071141 A1 | 3/2008 | Gattani et al. |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0243142 A1* | 10/2008 | Gildenberg ............ A61B 90/36 606/130 |
| 2008/0246771 A1 | 10/2008 | O'Neal |
| 2008/0253686 A1 | 10/2008 | Bayer |
| 2008/0262312 A1 | 10/2008 | Carroll |
| 2008/0269606 A1* | 10/2008 | Matsumura ............ A61B 8/12 600/438 |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |

(56) References Cited

U.S. PATENT DOCUMENTS

| | | |
|---|---|---|
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0260322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0069159 A1 | 3/2011 | Soler et al. |
| 2011/0084835 A1 | 4/2011 | Whitehouse |
| 2011/0105895 A1* | 5/2011 | Kornblau ............ A61B 34/20 600/426 |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2011/0301414 A1* | 12/2011 | Hotto ............. A61B 1/00055 600/114 |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0218024 A1 | 8/2013 | Boctor |
| 2013/0222640 A1 | 8/2013 | Baek |
| 2013/0253268 A1 | 9/2013 | Okada |
| 2013/0257778 A1 | 10/2013 | Rehe |
| 2013/0264465 A1 | 10/2013 | Dai |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0194732 A1 | 7/2014 | Nakaguchi |
| 2014/0212025 A1 | 7/2014 | Thienphrapa |
| 2014/0213850 A1 | 7/2014 | Levy |
| 2014/0225998 A1 | 8/2014 | Dai |
| 2014/0243658 A1 | 8/2014 | Breisacher et al. |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094538 A1 | 4/2015 | Wieth |
| 2015/0099925 A1 | 4/2015 | Tal Davidson et al. |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |
| 2016/0191887 A1* | 6/2016 | Casas ................ A61B 34/20 348/47 |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |

(56) References Cited

FOREIGN PATENT DOCUMENTS

| | | |
|---|---|---|
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988613 | 11/2008 |
| EP | 2023794 | 2/2009 |
| EP | 2023795 | 2/2009 |
| EP | 2190341 | 8/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2 550 908 A1 | 1/2013 |
| EP | 2550908 A1 | 1/2013 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| EP | 9991537 | 3/2016 |
| GB | 12196628 | 3/2015 |
| JP | H1043129 | 2/1998 |
| JP | H10239740 | 9/1998 |
| JP | 41137512 | 5/1999 |
| JP | 200161861 A | 3/2001 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007025081 A2 | 3/2007 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 A1 | 12/2010 |
| WO | 2012038958 | 3/2012 |
| WO | 2012056453 A2 | 5/2012 |
| WO | 2012075153 A2 | 6/2012 |
| WO | 2012077116 | 6/2012 |
| WO | 2012077117 A1 | 6/2012 |
| WO | 2012096102 | 7/2012 |
| WO | 2012120507 A1 | 9/2012 |
| WO | 2012149548 A2 | 11/2012 |
| WO | 2013014673 | 1/2013 |
| WO | 2013024476 | 2/2013 |
| WO | 2013165380 A2 | 11/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 20150318772 A2 | 3/2015 |
| WO | WO 2015/031877 A2 | 3/2015 |
| WO | WO 2015031877 * | 3/2015 ............. A61B 1/045 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 201511957341 | 8/2015 |
| WO | WO 2015/119573 A1 | 8/2015 |
| WO | WO 2015119573 * | 8/2015 ............... A61B 1/00 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |
| WO | 2015047631 | 4/2016 |

OTHER PUBLICATIONS

Notice of Allowance dated Apr. 16, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/986,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Notice of Allowance dated May 25, 2017 for U.S. Appl. No. 14/318,189.
Office Action dated May 23, 2017 for U.S. Appl. No. 14/500,975.
International Search Report for PCT/US14/37004, dated Sep. 25, 2014.
International Search Report for PCT/US14/38094, dated Nov. 6, 2014.

(56) References Cited

OTHER PUBLICATIONS

International Search Report for PCT/US2014/037526, dated Oct. 16, 2014.
International Search Report for PCT/US2014/071085, dated Mar. 27, 2015.
International Search Report for PCT/US2014/58143, dated Jan. 21, 2015.
International Search Report for PCT/US2015/012596, dated Dec. 11, 2015.
International Search Report for PCT/US2015/012751, dated Jun. 26, 2015.
International Search Report for PCT/US2015/027902, dated Jul. 23, 2015.
International Search Report for PCT/US2015/28962, dated Jul. 28, 2015.
International Search Report for PCT/US2015/29421, dated Aug. 7, 2015.
International Search Report for PCT/US2015/41396, dated Sep. 29, 2015.
International Search Report for PCT/US2015/47334, dated Dec. 28, 2015.
International Search Report for PCT/US2015/6548, dated Feb. 26, 2016.
International Search Report for PCT/US2015/66486, dated Dec. 17, 2015.
International Search Repor for PCT/US2016/058915, dated Feb. 15, 2017.
Corrected Notice of Allowance dated Apr. 13, 2016 for U.S. Appl. No. 13/680,646.
Office of Allowence dated Mar. 28, 2016 for U.S. Appl. N0. 13/413,059.
Notice of Allowance dated Mar. 29, 2016 for U.S. Appl. No. 13/680,646.
Office Action dated Feb. 26, 2016 for U.S. Appl. No. 14/274,323.
Office Action dated Feb. 4, 2016 for U.S. Appl. No. 14/271,234.
Office Action dated Mar. 23, 2016 for U.S. Appl. No. 13/713,449.
Office Action dated Mar. 24, 2016 for U.S. Appl. No. 13/212,627.
Office Action dated Mar. 28. 2016 for U.S. Appl. No. 13/119,032.
Office Action dated May 25, 2016 for U.S. Appl. No. 14/271,234.
Offce Action dated May 5, 2016 for U.S. Appl. No. 14/278,338.
Office Action dated May 6, 2016 for U.S. Appl. No. 14/263,896.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Heat; Plastics Technology, Jun. 2001—article obtained online from http://www.ptonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,883.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,336.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2417 for U.S. Appl. No. 14/276,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.

* cited by examiner

DEVICE AND METHOD FOR TRACKING THE POSITION OF AN ENDOSCOPE WITHIN A PATIENT'S BODY

CROSS-REFERENCE TO RELATED APPLICATIONS

This application is a continuation of U.S. Nonprovisional patent application Ser. No. 15/335,249 filed Oct. 26, 2016, which claims the benefit of U.S. Provisional Application No. 62/247,232, filed on Oct. 28, 2015.

The present specification relates to United States Patent Application Publication Number US 2015/0099925 A1, entitled "Endoscope With Integrated Sensors", and published on Apr. 9, 2015; and to United States Patent Application Publication Number US 2015/0313445 A1, entitled "System And Method Of Scanning A Body Cavity Using a Multiple Viewing Elements Endoscope", and published on Nov. 5, 2015.

The above-mentioned applications are herein incorporated by reference in their entirety.

FIELD

The present specification relates generally to endoscopes, and more specifically, to a device and method for displaying an image of a position of an endoscope within a patient's body, superimposed on the patient's body or overlaid on an image of the patient's body.

BACKGROUND

An endoscope is a medical instrument used for examining and treating internal body cavities such as the alimentary canals, airways, the gastrointestinal system, and other organ systems. Conventional endoscopes are usually an elongated tubular shaft, rigid or flexible, having a video camera and a fiber optic light guide for directing light from an external light source situated at a proximal end of the tube to a distal tip. Also, most endoscopes are provided with one or more channels, through which medical devices, such as forceps, probes, and other tools, may be passed. Further, during an endoscopic procedure, fluids, such as water, saline, drugs, contrast material, dyes, or emulsifiers are often introduced or evacuated via the shaft. A plurality of channels, one each for introduction and suctioning of liquids, may be provided within the shaft.

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper gastrointestinal (GI) endoscopy among others. Endoscopes may be inserted into the body's natural orifices or through an incision in the skin.

Some endoscopes have viewing elements for viewing an internal organ, such as the colon, and an illuminator for illuminating the field of view of the viewing elements. The viewing elements and illuminators are located in a tip of the endoscope and are used to capture images of the internal walls of the body cavity being endoscopically scanned. The captured images are sent to a control unit coupled with the endoscope via one of the channels present in the scope shaft, for being displayed on a screen coupled with the control unit.

During an endoscopic procedure an operating physician guides the endoscope within a patient's body by using the captured images displayed on the screen coupled with the control unit as a guide. However, the physician does not know the exact position of the endoscope within the body with respect to the internal organs of the patient. The physician maneuvers the endoscope largely based on his/her knowledge of the patient's anatomy, experience and the displayed images of internal organs.

Conventional endoscope guiding systems allow an operating physician to view the scope's position within a patient's body, by displaying a representation of the endoscope within the body during an endoscopic procedure. However, such representations depict the scope's position with respect to the endoscope's coordinate system and not with respect to the patient's coordinates. Thus the operator is not provided with an accurate sense of the scope's position relative to the patient's body. This may cause the operator to maneuver the scope in such a manner that causes discomfort or even pain to the patient.

Hence, there is need for a device and method that displays an accurate position of an endoscope within a patient's body by combining the scope's coordinates with the patient's coordinate. There is need for a method of combining patient and endoscope information to provide an augmented reality environment clearly highlighting the endoscope's position with respect to a patient's internal organs.

SUMMARY

The following embodiments and aspects thereof are described and illustrated in conjunction with systems, tools and methods, which are meant to be exemplary and illustrative, not limiting in scope.

The present specification discloses an endoscope system having an endoscope handle and an endoscope body adapted to be inserted into a gastrointestinal tract of a patient, the system comprising: a plurality of orientation markers positioned on said endoscope handle, wherein said orientation markers are distributed around a circumference of said endoscope handle; a plurality of sensors positioned at different locations longitudinally along an external surface of the endoscope body, wherein each of said plurality of sensors is adapted to generate first orientation data; one or more cameras positioned external to said patient and adapted to detect one or more of said plurality of orientation markers and generate second orientation data; and a controller adapted to receive said first orientation data and second orientation data and generate data indicative of a position of said endoscope body within said gastrointestinal tract of the patient.

Optionally, the data indicative of a position of said endoscope body includes positions of all of the endoscope body that has entered into the gastrointestinal tract of the patient.

Optionally, the sensors are distributed longitudinally along a length of the endoscope body and are separated by a predefined distance of at least 0.1 mm.

Optionally, the controller is adapted to generate an image of said endoscope body based upon data indicative of a position of said endoscope body.

Optionally, the controller is further adapted to orient said image by performing a translation of an orientation of the endoscope to a coordinate system defining a position of said patient and applying said translation to the said image.

Optionally, the controller is further adapted to overlay said oriented image onto an image of a portion of said patient's gastrointestinal tract to generate an oriented, overlaid image of said endoscope body.

Optionally, the first orientation data is indicative of a position of the endoscope body relative to an endoscope coordinate system.

Optionally, the second orientation data is indicative of a position of the endoscope handle relative to a patient coordinate system.

Optionally, the endoscope system further comprises a projector adapted to receive the oriented, overlaid image of said endoscope body from the controller and project it onto the patient.

Optionally, the plurality of orientation markers comprise spheres placed on handle of the endoscope, each sphere having a diameter ranging from 0.5 to 2 cm.

Optionally, the plurality of orientation markers comprise pinpoint-sized laser beams.

Optionally, the plurality of orientation markers are made of a material that reflects or emits infra-red light.

Optionally, the plurality of sensors comprise one or more of accelerometers, gyroscopes, magnetometers and stripes that measure the bending and twisting of an insertion tube of the endoscope by one or more of electro-optic and mechanic methods.

Optionally, the plurality of sensors comprise one or more of inductive sensors, capacitive sensors, capacitive displacement sensors, photoelectric sensors, magnetic sensors, and infrared sensors placed along one of an elongated shaft and an insertion tube of the endoscope, wherein each of the sensors corresponds to a unique identifier, based on the location of the sensor along the insertion tube.

Optionally, the endoscope system further comprising a distance sensor adapted to detect distance markers positioned at different locations longitudinally along an external surface of the endoscope body and generate distance data, wherein the distance sensor comprises one or more of a depth sensor and a touch sensor for providing a distance the insertion tube has travelled inside the gastrointestinal tract of a patient.

Optionally, the endoscope system comprises two stereo-calibrated cameras adapted to generate second orientation data comprising 3D location of the fiducials in the cameras' own coordinate system by triangulation.

The present specification also discloses a method of tracking the position of an endoscope within a patient's organ during an endoscopic procedure, the method comprising: determining a position of the endoscope within the organ in the endoscope's coordinate system; capturing in an image a plurality of fiducial markers by an external optical tracker; transforming the captured fiducial markers from the endoscope's coordinate system to the optical tracker's coordinate system; detecting the captured fiducial markers on a model of the patient's organ; and projecting the image of the endoscope with the fiducial markers upon an image of the patient's organ with the fiducial markers.

Optionally, the external optical tracker is a camera placed above the endoscope performing the endoscopic procedure.

Optionally, the captured fiducial markers are detected on a model of the patient's organ by using an object detection algorithm. Still optionally, the captured fiducial markers are detected on a model of the patient's organ by using the Hough Transform. Optionally, the method further comprises casting the position of the endoscope directly on the patient's body by using a calibrated projector.

The present specification also discloses an endoscopy system for tracking the position of an endoscope within a patient's organ during an endoscopic procedure, the system comprising at least an endoscope coupled with a plurality of fiducial markers; an optical tracker placed external to the endoscope and a computing unit for at least processing the images captured by the optical tracker, the optical tracker capturing in an image the plurality of fiducial markers and the endoscope during the endoscopic procedure, the computing unit transforming the captured fiducial markers from the endoscope's coordinate system to the optical tracker's coordinate system and projecting the image of the endoscope with the fiducial markers upon an image of the patient's organ with the fiducial markers.

Optionally, the external optical tracker is a camera placed above the endoscope performing the endoscopic procedure.

Optionally, the captured fiducial markers are transformed from the endoscope's coordinate system to the optical tracker's coordinate system by using an object detection algorithm. Still optionally, the captured fiducial markers are transformed from the endoscope's coordinate system to the optical tracker's coordinate system by using the Hough Transform.

Optionally, the system further comprises a calibrated projector for casting the position of the endoscope directly on the patient's body.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein.

DETAILED DESCRIPTION

Figure 1A:
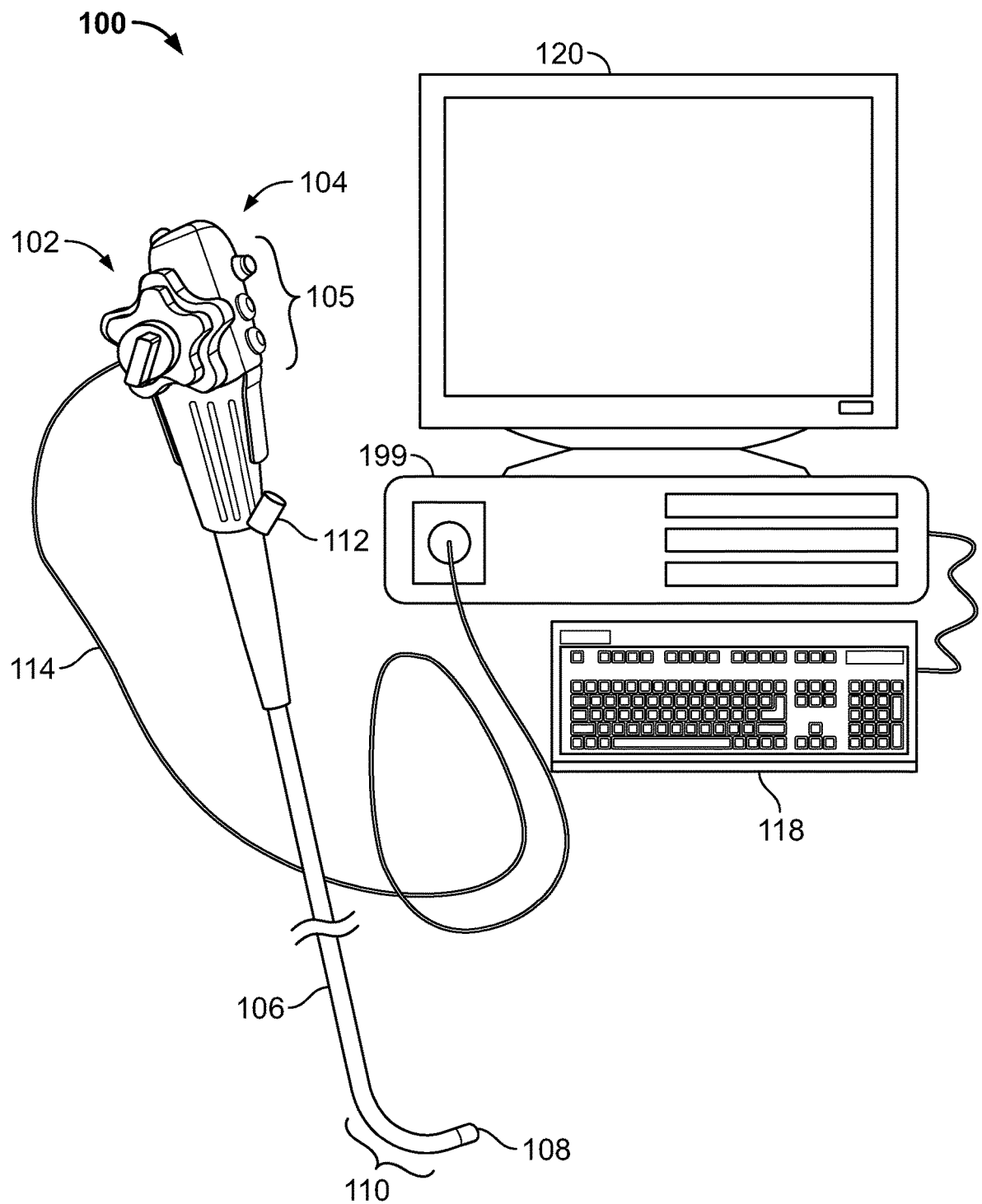
FIG. 1A illustrates a multiple viewing elements endoscopy system in which the methods of the present specification may be implemented.

The present specification provides a method for displaying the position of an endoscope within a patient's body. In an embodiment, an image of the endoscope, being used in an endoscopic procedure is projected directly over the patient's body allowing an operating physician to clearly ascertain the position of the endoscope within the body. In another embodiment, the endoscope's position within a patient's body is displayed as an image along with an image of the patient's internal organs on a monitor allowing the operator to maneuver the endoscope easily within the body.

In various embodiments, the method of the present specification allows an operating physician to accurately determine the position of an endoscope within a patient's body during an endoscopic procedure, thereby reducing endoscope navigation time significantly. The method also allows the operator to correctly ascertain the distance of the endoscopic tip from a patient's cecum during a GI procedure.

In an embodiment, the method of the present specification allows for a three-dimensional reconstruction of a patient's colon. The images captured during an endoscopic procedure may be displayed on top of the colon model enabling better maneuverability of the endoscope and an improved diagnosis of the colon.

It is noted that the term "endoscope" as mentioned herein may refer particularly to a colonoscope, according to some embodiments, but is not limited only to colonoscopes. The term "endoscope" may refer to any instrument used to examine the interior of a hollow organ or cavity of the body.

It should also be noted that a plurality of terms, as follows, appearing in this specification are used interchangeably to apply or refer to similar components and should in no way be construed as limiting:

"Utility tube/cable" may also be referred to as an "umbilical tube/cable".
A "main control unit" may also be referred to as a "controller unit" or "main controller".
A "viewing element" may also be referred to as an image capturing device/component, viewing components, camera, TV camera or video camera.
A "working channel" may also be referred to as a "service channel".
An "illuminator" may also be referred to as an "illumination source", and in some embodiments, an LED.
A "flexible shaft" may also be referred to as a bending section or vertebra mechanism.
"Fiducial", used herein and throughout, may be used to refer to a standard or reference, for example, a fiducial marker.

As used in the specification, the term "optical assembly" is used to describe a set of components that allows the endoscopic device to capture light and transform that light into at least one image. In some embodiments, lenses/optical elements are employed to capture light and image capturing devices, such as sensors, are employed to transform that light into at least one image.

Image capturing devices may be Charged Coupled Devices (CCD's) or Complementary Metal Oxide Semiconductor (CMOS) image sensors, or other suitable devices having a light sensitive surface usable for capturing an image. In some embodiments, a sensor such as a Charge Coupled Device (CCD) or a Complementary Metal Oxide Semiconductor (CMOS) image sensor (for detecting the reflected light received by an optical element), is employed.

In some embodiments, an optical element comprises a plurality of optics such as lens assemblies, lenses and protective glass, and is configured to receive reflected light from target objects.

In accordance with an embodiment of the present specification, a tip cover may house the tip section of an endoscope. The tip section, with the tip cover, may be turned or maneuvered by way of a flexible shaft, which may also be referred to as a bending section, for example, a vertebra mechanism. Tip cover may be configured to fit over the inner parts of the tip section, including an electronic circuit board assembly and a fluid channeling component, and to provide protection to the internal components in the inner parts, such as a body cavity. The endoscope can then perform diagnostic or surgical procedures inside the body cavity. The tip section carries one or more viewing elements, such as cameras, to view areas inside body cavities that are the target of these procedures.

Tip cover may include panels having a transparent surface, window or opening for optical lens assemblies of viewing elements. The panels and viewing elements may be located at the front and sides of the tip section. Optical lens assemblies may include a plurality of lenses, static or movable, providing different fields of view.

An electronic circuit board assembly may be configured to carry the viewing elements, which may view through openings on the panels. Viewing elements may include an image sensor, such as but not limited to a Charge Coupled Device (CCD) or a Complementary Metal Oxide Semiconductor (CMOS) image sensor.

The electronic circuit board assembly may be configured to carry illuminators that are able to provide illumination through illuminator optical windows. The illuminators may be associated with viewing elements, and may be positioned to illuminate the viewing elements' fields of view.

The present specification provides a method of determining the position of an endoscope within a patient's body by determining the endoscope's coordinates within the body. In an embodiment, the present specification discloses the use of fiducial markers or points to track the position of an endoscope within a patient's body. In an embodiment, fiducial markers are distributed around the entirety of the endoscope's handle and in conjunction with a sensing system provide data describing how the handle has been turned or oriented in 3D space. In an embodiment, a camera system is used to capture the position of the fiducial markers and, using known algorithms, the orientation of the endoscope is translated relative to the camera system. In an embodiment, fixing the position of the patient and the camera system enables the camera system to scale and translate the orientation of the endoscope into an image which is projected onto the body of the patient.

In embodiments, the position of an endoscope within a patient's body is tracked by sensors that measure the bending, turning, or orientation of the endoscope body within the patient's body. In other embodiments, sensors are integrated along the endoscope's insertion tube to provide real-time information on the distance being travelled by the endoscope inside the patient's body. In an embodiment, the orientation of the endoscope obtained from the fiducial markers and the bending, turning, or orientation information obtained via the sensors together provides a precise orientation of the entire endoscope within the patient. In an embodiment, position of a first position of the endoscope is determined by using the fiducial markers and, the position of each point along the endoscope body is determined by using a turn or orientation change relative to the endoscope's handle and the distance that point has traveled in the patient's body.

The present specification is directed towards multiple embodiments. The following disclosure is provided in order to enable a person having ordinary skill in the art to practice the specification. Language used in this specification should not be interpreted as a general disavowal of any one specific embodiment or used to limit the claims beyond the meaning of the terms used therein. The general principles defined herein may be applied to other embodiments and applications without departing from the spirit and scope of the specification. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the specification have not been described in detail so as not to unnecessarily obscure the present specification.

It should be noted herein that any feature or component described in association with a specific embodiment may be used and implemented with any other embodiment unless clearly indicated otherwise.

Reference is now made to FIG. 1A, which shows a multi-viewing elements endoscopy system 100. System 100 may include a multi-viewing elements endoscope 102. Multi-viewing elements endoscope 102 may include a handle 104, from which an elongated shaft 106 emerges. Elongated shaft 106 terminates with a tip section 108 which is turnable by way of a bending section 110. Handle 104 may be used for maneuvering elongated shaft 106 within a body cavity. The handle may include one or more buttons and/or knobs and/or switches 105 which control bending section 110 as well as functions such as fluid injection and suction. Handle 104 may further include at least one, and in some embodiments, one or more working channel openings 112 through which surgical tools may be inserted as well as one and more side service channel openings.

A utility cable 114, also referred to as an umbilical tube, may connect between handle 104 and a Main Control Unit 199. Utility cable 114 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 199 contains the controls required for displaying the images of internal organs captured by the endoscope 102. The main control unit 199 may govern power transmission to the endoscope's 102 tip section 108, such as for the tip section's viewing elements and illuminators. The main control unit 199 may further control one or more fluid, liquid and/or suction pump(s) which supply corresponding functionalities to the endoscope 102. One or more input devices 118, such as a keyboard, a touch screen and the like may be connected to the main control unit 199 for the purpose of human interaction with the main control unit 199. In the embodiment shown in FIG. 1, the main control unit 199 comprises a screen/display 120 for displaying operation information concerning an endoscopy procedure when the endoscope 102 is in use. The screen 120 may be configured to display images and/or video streams received from the viewing elements of the multi-viewing element endoscope 102. The screen 120 may further be operative to display a user interface for allowing a human operator to set various features of the endoscopy system.

In various embodiments, the position of an endoscope within a patient's body is calculated by determining the endoscope's coordinates within the body. Various methods may be used for determining the location and pose of the endoscope within the scope's coordinate system or relative to an exterior coordinate system.

In an embodiment, the present specification discloses the use of fiducial markers or points to track the position of an endoscope within a patient's lumen. As is commonly known in the art, a fiducial marker or fiducial point is an object placed in the field of view of an imaging system which appears in the image produced, for use as a point of reference or a measure. It may be either something placed into or on the imaging subject, or a mark or set of marks in the reticle of an optical instrument. The location of the fiducial markers is dependent upon the method used to compute the scope's pose within the patient's body.

In an embodiment, the fiducial markers or points are small spheres (balls) placed on an endoscope's handle that enable measurement of the endoscope's position relative to the endoscope's coordinates (internal coordinate system). These spheres are easily recognizable in an image. Other recognizable shapes, such as but not limited to crosses, for example, may also be used as fiducial markers. In an embodiment, the fiducial markers employed in the present specification are spheres having a diameter in the range of 0.5 to 2 cm. In another embodiment, pinpoint-sized laser beams may also be used as fiducial markers as they are capable of being uniquely detected by an optical tracker/camera, when in the field of view of the optical tracker/camera. Fiducial markers may be made of any material that enables easy detection by optical trackers. In an embodiment, the fiducial markers may be made of a material that reflects or emits any form of light, particularly infrared light. A plurality of optical trackers, such as cameras, may be employed for detecting fiducial points on the handle portion of the endoscope. The fiducial points appear in the image captured by the optical trackers serving as points of reference for co-relating the endoscope's coordinates with the coordinates of the optical tracker.

In embodiments, the optical tracker, which may be an external camera, is placed above a patient undergoing an endoscopic procedure, so that the camera captures both the endoscope and the patient's body in the same image. Fiducial markers are placed on at least a portion of the endoscope. Hence external camera produces an image that displays the fiducial markers on the (partially unseen) endoscope along with the patient's body.

In an embodiment of the present specification, electromagnetic tracking techniques are used to detect the position of an endoscope within a patient's body. As is known in the art, for electromagnetic tracking of an endoscope, a plurality of electromagnetic coils is wound around one or more portions of the endoscope. The coils emit an electromagnetic signal that can be detected by an electromagnetic tracking device placed external to the endoscope. In an embodiment, fiducial markers are attached to the electromagnetic tracking device which is used to measure the position of the endoscope with respect to the coordinates of the tracking device.

Sensing Systems:

In another embodiment of the present specification, the position of an endoscope within a patient's body is tracked by sensors that measure the orientation of the insertion tube of the endoscope at several positions. In various embodiments, sensors such as accelerometers, gyroscopes, magnetometers (i.e. electronic compasses) and stripes that measure the bending and twisting of the insertion tube by electro-optic/mechanic methods may be used. In accordance with another embodiment, the endoscope comprises sensors integrated along its insertion tube to provide real-time information on the distance being travelled by the endoscope inside the patient's lumen.

In one embodiment, a plurality of sensors are placed along the elongated shaft or insertion tube of the endoscope. Further, each sensor has a unique identifier, code, signature, or other identification according to its location (such as distance from the distal tip) along the insertion tube. In another embodiment, each identifier is not only unique to the sensor but also indicative of the particular position, or distance, occupied by the sensor. Several different types of sensors may be employed, including, but not limited to inductive sensors, capacitive sensors, capacitive displacement sensors, photoelectric sensors, magnetic sensors, and infrared sensors. In an embodiment, a depth sensor is placed at the entrance of the body where the endoscope is inserted and is in communication with the main control unit that is used with the endoscope. In some embodiments a matrix of sensors are employed, so that continuity in reading of distances is achieved. In some embodiments touch sensors may be used. Thus, for example, with touch sensors placed at regular intervals on the insertion tube, the number of touch sensors showing an output would indicate the depth the insertion tube has travelled inside the lumen of the body.

It is known in the art that the insertion tube has numbers or marks on it to indicate to the physician the distance of the insertion tube within patient body. Thus, in another embodiment, an imaging device, such as a CCD, a CMOS and the like, is placed outside the patient's body, close to the entrance point of the insertion tube of the endoscope to capture images of the mark of the insertion tube visible outside the body, thereby providing the distance of the insertion tube within patient body.

In a yet another embodiment, depth is measured by using sensors that respond to the physician's grip on the tube. Sensors are placed over substantially the entire length of the insertion tube, and each sensor has a unique identifier, code, signature, or other identification per its location along elongated axes of the insertion tube. Methods and systems of determining the location or distance of an endoscopic tip within a patient's body are described in co-pending United States Patent Application Publication Number US 2015/0099925 A1, entitled "Endoscope with Integrated Sensors" and published on Apr. 9, 2015, which is herein incorporated by reference in its entirety. Hence, as described above various methods may be used for determining the location and pose of the endoscope within the scope's coordinate system.

Orientation Determination:

The 3D coordinates of the endoscope can be reconstructed from its computed orientations by integration by means of a bending matrix. A bending matrix provides a measurement of the extent of bending of an endoscope. The 3D coordinates of the endoscope can be reconstructed from the bending information provided by the bending matrix. In an embodiment, fiducial markers with known coordinates in both the endoscope's and the optical tracker's coordinate systems are used to obtain a match between the two coordinate systems.

In an embodiment, a 3D scope model is projected onto a two-dimensional (2D) plane by an optical tracker/camera. The optical tracker captures fiducial markers with respect to the camera's coordinates and matches the fiducial markers up to a model of a human organ being endoscopically scanned, such as a colon, in accordance with an embodiment of the present specification. An object detection algorithm is used to detect the captured fiducial markers within the frame/model of the patient's organ. In an embodiment, detected fiducial markers are represented with a circle or demarcations (in this case, orange) around the fiducial markers.

The transformation method for transforming the fiducial markers from the endoscope's coordinates to the optical tracker's coordinates is dependent on the optical tracker's characteristics. If the optical tracker is composed of two stereo-calibrated cameras, then these cameras compute the 3D location of the fiducials in their own coordinate system by triangulation. The transformation of these 3D points with the known 3D structure of the fiducial markers can be computed by any point-cloud registration algorithm such as Horn's algorithm which computes a transformation that minimizes the average distance between points. However, if the optical tracker is composed of a single camera, then the transformation can be computed by any algorithm that solves the PnP problem, such as EPnP, DLT, and POSSIT. As is known in the art, the PnP problem aims to determine the location of a camera based on comparison between a set of 3D points with known location in some arbitrary coordinate system, and their 2D projection by the camera.

In an embodiment, an object detection algorithm such as 'Hough Transform' is used to detect the captured fiducial markers within a frame/model of the patient's internal organ(s). In some embodiments, various other object detection algorithms may also be used. Hough transform is an algorithm that is commonly used to detect parametric shapes in images. For example it can be used to detect spheres. The algorithm first computes the number of pixels that are consistent with any parametric combination of a shape and second, determines a threshold value for the computed matrix.

In other embodiments data obtained from sensors such as accelerometers, gyroscopes, magnetometers (i.e. electronic compasses) and stripes placed along the insertion tube of the endoscope for measuring the bending and twisting of the insertion tube by electro-optic/mechanic methods may be used to obtain distance being travelled by the endoscope inside the patient's lumen. In an embodiment, distance being travelled by the endoscope inside the patient's lumen is obtained by using data obtained from sensors such as inductive sensors, capacitive sensors, capacitive displacement sensors, photoelectric sensors, magnetic sensors, depth sensors, infrared sensors and touch sensors placed along the elongated shaft or insertion tube of the endoscope. A unique identifier of each of these sensors provides information about the particular position (location with respect to a distal tip of the insertion tube), or distance, occupied by the sensor, thereby providing an orientation of the scope within the patient's organ.

Image Projection

In embodiments, the orientation of the endoscope determined by using the fiducial markers and the sensors is translated to the camera's coordinate system, scaled based on the patient position and size and the relative camera position, and projected onto the patient.

In an embodiment, the captured fiducial markers are projected on an image of the patient's internal organ. A 3D image of the internal organ displaying the captured fiducial markers is obtained by using computer software. In another embodiment, the captured fiducial markers corresponding to the endoscope are projected on an image of the endoscope. A 3D image of the endoscope displaying the captured fiducial markers is obtained by using computer software. In yet another embodiment, the image of the internal organ along with the fiducial markers and the image of the endoscope with the fiducial markers are displayed together to enable an operating physician to clearly determine the position of the endoscope within the organ.

In an embodiment, a projector connected to the control unit of the endoscope is used to project a virtual model of the patient's organ being scanned, showing a position of the endoscope therein, directly on the patient's body. In an embodiment, the projector is calibrated to convey its position in relation to the positions of the endoscope and the patient in the coordinate system of the endoscope and the patient. Calibration also provides the internal parameters of the projector, such as the direction of rays originating from the projector and the patient. By using the internal parameters, the exact illumination pattern of the projector may be computed, which in turn enables real time projection of a virtual model (holographic) of the endoscope's location within the patient's body on top of the patient.

Figure 1B:
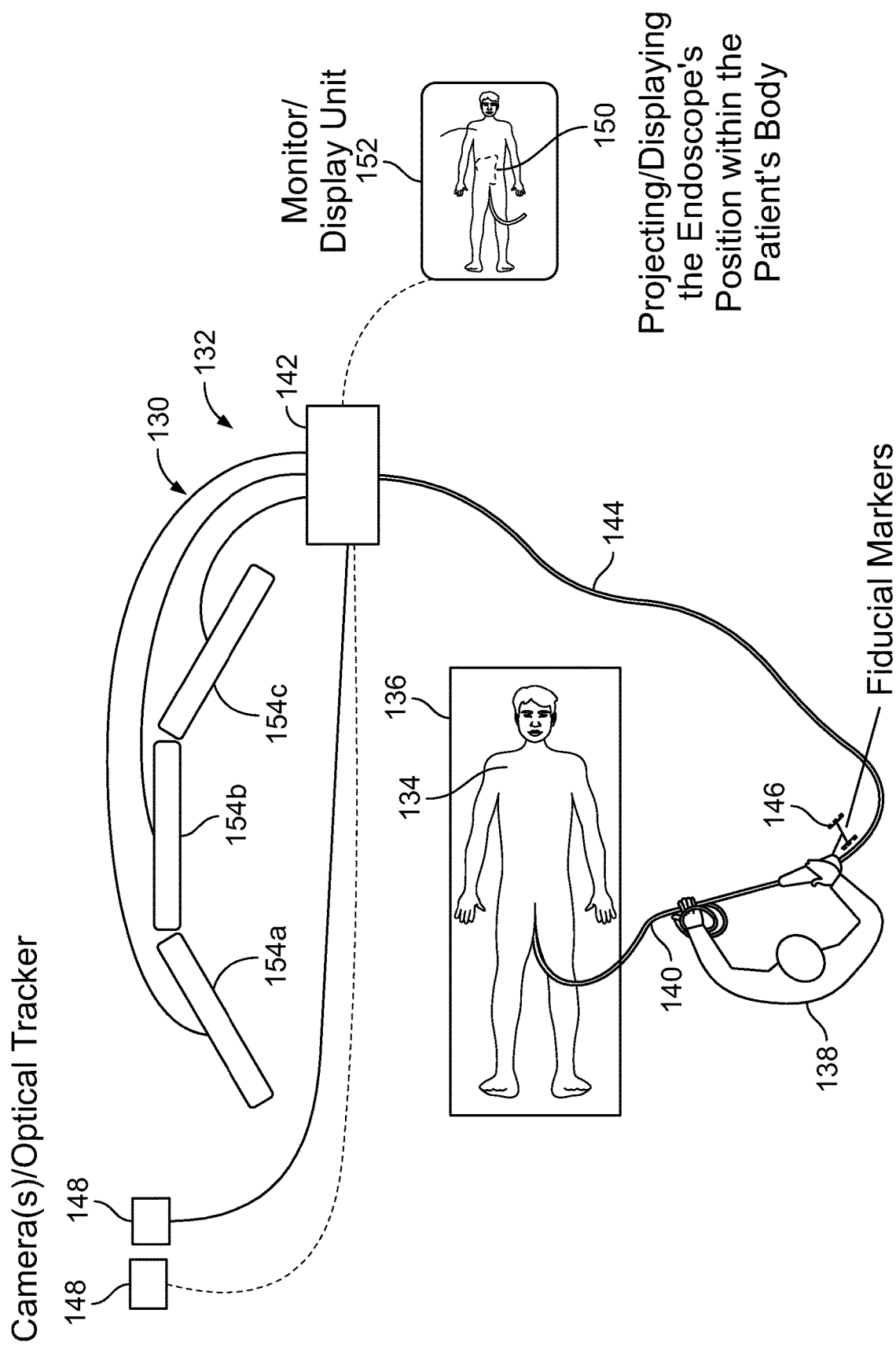
FIG. 1B is a schematic depiction of a layout of a multiple viewing elements endoscopy system and an associated interface unit deployed in an operating room in which the methods of the present specification may be implemented.

FIG. 1B schematically depicts a layout of an endoscope system 130 and an associated interface unit 132 deployed in an operating room, in which the optical trackers and fiducial markers as described above, may be employed. A patient 134 is supported on a bed 136 while a physician 138 is using an endoscope portion 140 of endoscope system 130 in an endoscopic procedure. Endoscope 140 is connected to a main controller 142 by a utility cable 144. A plurality of fiducial markers 146 are provided on the endoscope 140. Optical tracker, or external camera 148, is placed above the patient 134 so that the camera 148 captures the endoscope 140, fiducial markers 146 and the patient's body 134 in the same image 150 displayed on an external display unit 152. In another embodiment more than one optical tracker, or external camera 148, may be positioned above patient 134.

Thus, the optical tracker, or in this case external camera, is placed above a patient undergoing an endoscopic procedure, so that the camera captures both the endoscope and the patient's body in the same image. Fiducial markers are placed on at least a portion of the endoscope. Hence external camera produces an image that displays the fiducial markers on the (partially unseen) endoscope along with the patient's body. Next, an object detection algorithm such as 'Hough Transform' is used to detect the captured fiducial markers (described in detail with respect to FIG. 3) within a frame/model of the patient's internal organ. In various embodiments, after determining the external camera's parameters (by calibration) a virtual model of the patient's organ (e.g. colon) is rendered on top of the patient image taken by the external camera. In an embodiment, the virtual model of the patient's organ showing the position of the endoscope is cast directly on the patient's body by using a calibrated projector.

Endoscope 140 provides one or more endoscopic views (which may be simultaneous) using one, two, three or more cameras housed in the tip of endoscope 140. Main controller 142 is connected to at least one display screen 154 (not shown) or a plurality of display screens, for example three display screens 154a, 154b, and 154c, respectively, wherein each display screen is configured to display a corresponding view of the three endoscopic views provided by endoscope system 130. Display screen/s 154 is positioned facing physician 138 and possibly elevated so that physician 138 may conduct the endoscopic procedure by looking at the screen displays and having an undisturbed line of sight thereto. In an embodiment, the scope location and pose is determined relative to an exterior coordinate system. In this embodiment, the fiducial markers are attached to the exterior coordinate tracking system.

Figure 1C:
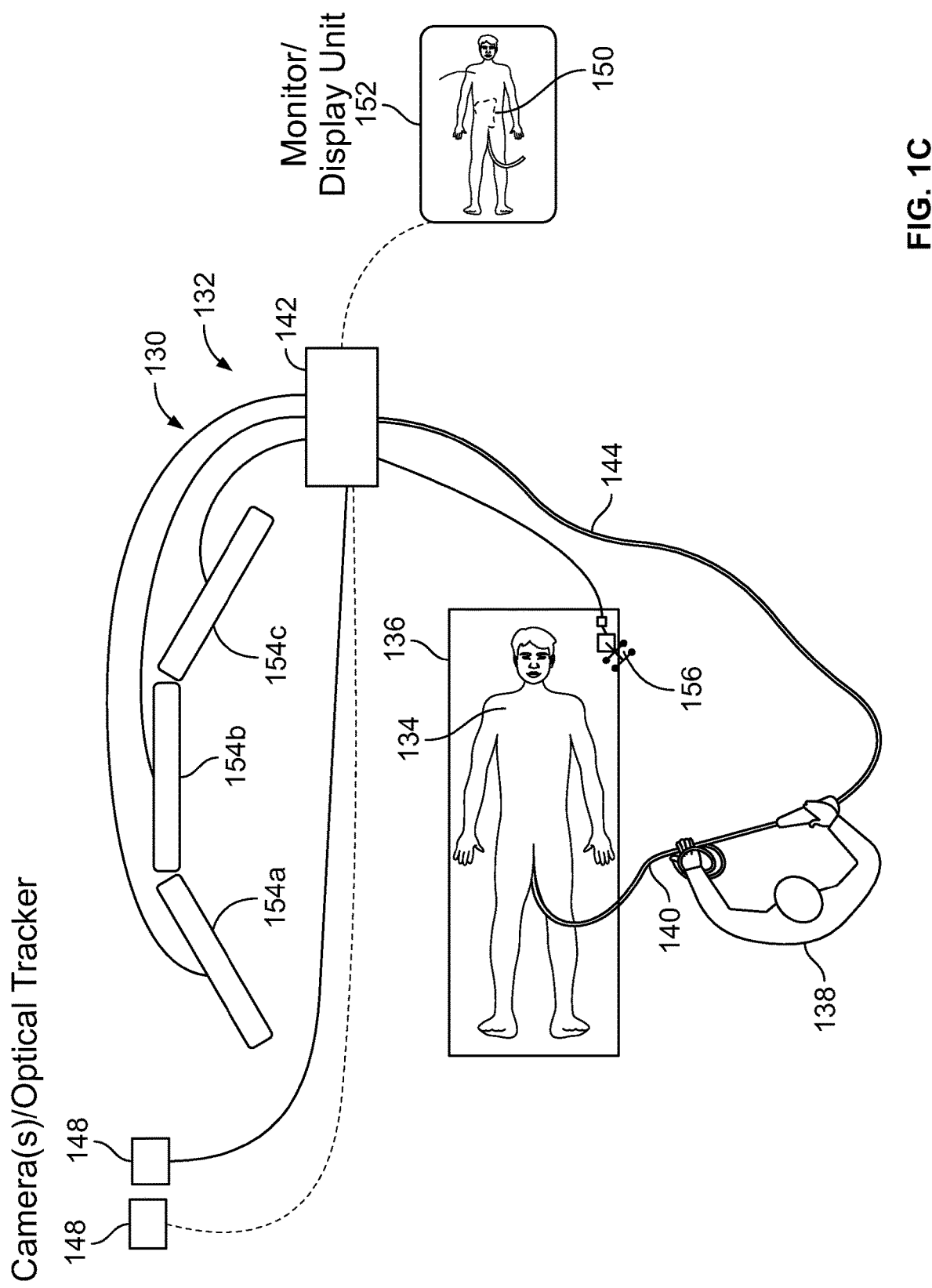
FIG. 1C is a schematic diagram of another layout of a multiple viewing elements endoscopy system and an associated interface unit deployed in an operating room in which the methods of the present specification may be implemented.

FIG. 1C illustrates an electromagnetic field generator with fiducial markers placed in proximity to the patient undergoing an endoscopy procedure as shown in FIG. 1B. An electromagnetic field generator with fiducial markers 156 is placed in close proximity to the patient 134, for example on/under patient bed 136 or on a stand (not shown) placed in proximity to patient 134.

Figure 1D:
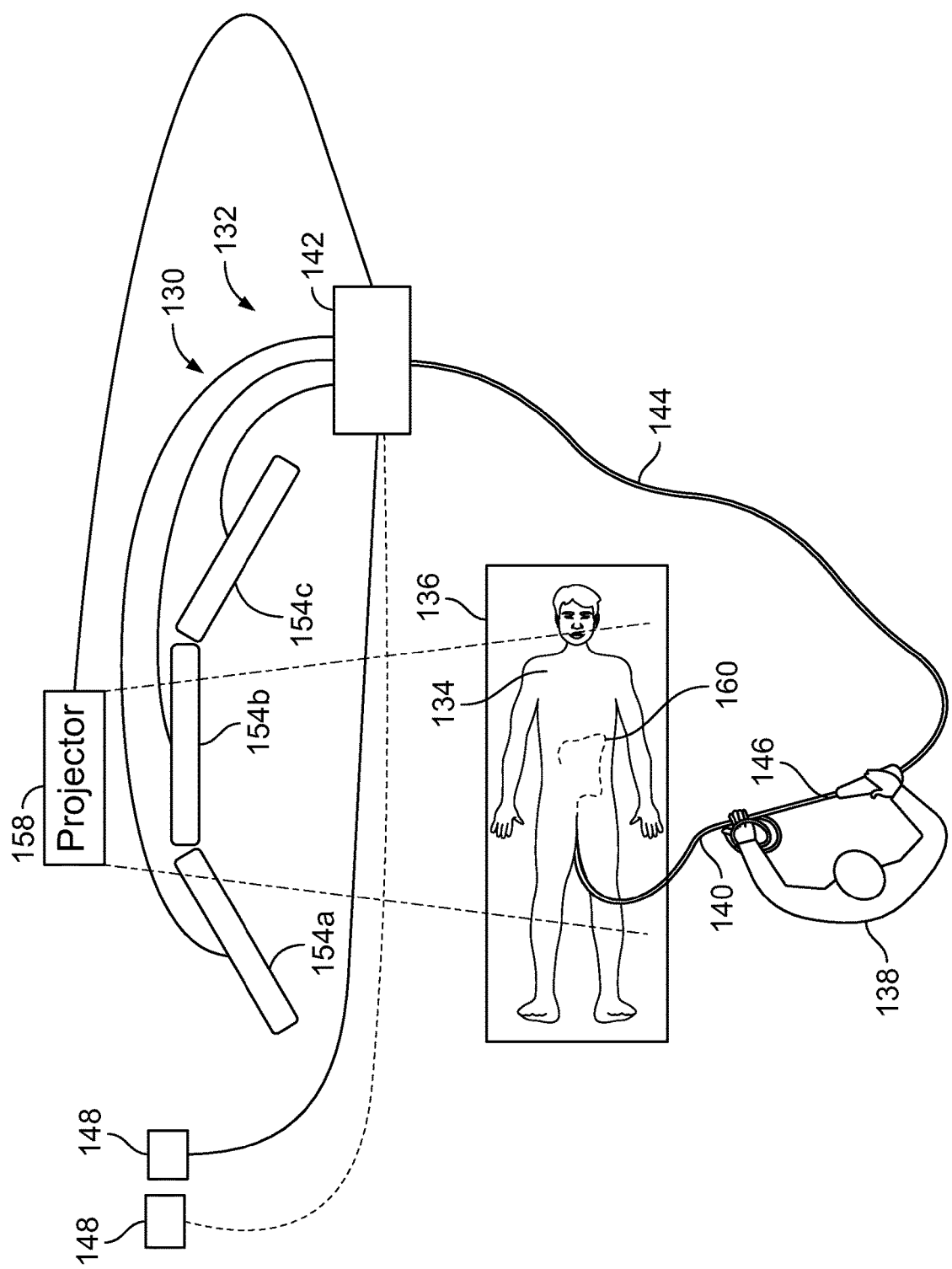
FIG. 1D is a schematic diagram of yet another layout of a multiple viewing elements endoscopy system and an associated interface unit deployed in an operating room in which the methods of the present specification may be implemented.

FIG. 1D illustrates the position of the endoscope within the body of the patient undergoing an endoscopic procedure as shown in FIG. 1B being cast directly on the patient's body by using a projector, in accordance with an embodiment of the present specification. As shown a projector 158 connected to the controller 142 is used to project a virtual model 160 of the patient's colon showing a position of the endoscope therein, directly on the patient's body 134. In an embodiment, the projector 158 is calibrated, whereby calibrating the projector 158 conveys its position in relation to the positions of the endoscope 140 and the patient 134 in the coordinate system of the endoscope and the patient. Calibration also provides the internal parameters of the projector 158, such as the direction of rays originating from the projector and the patient 134. By using the internal parameters, the exact illumination pattern of the projector 158 may be computed, which in turn enables real time projection of a virtual model 160 (holographic) of the endoscope's 140 location within the patient's body on top of the patient 134.

Figure 2:
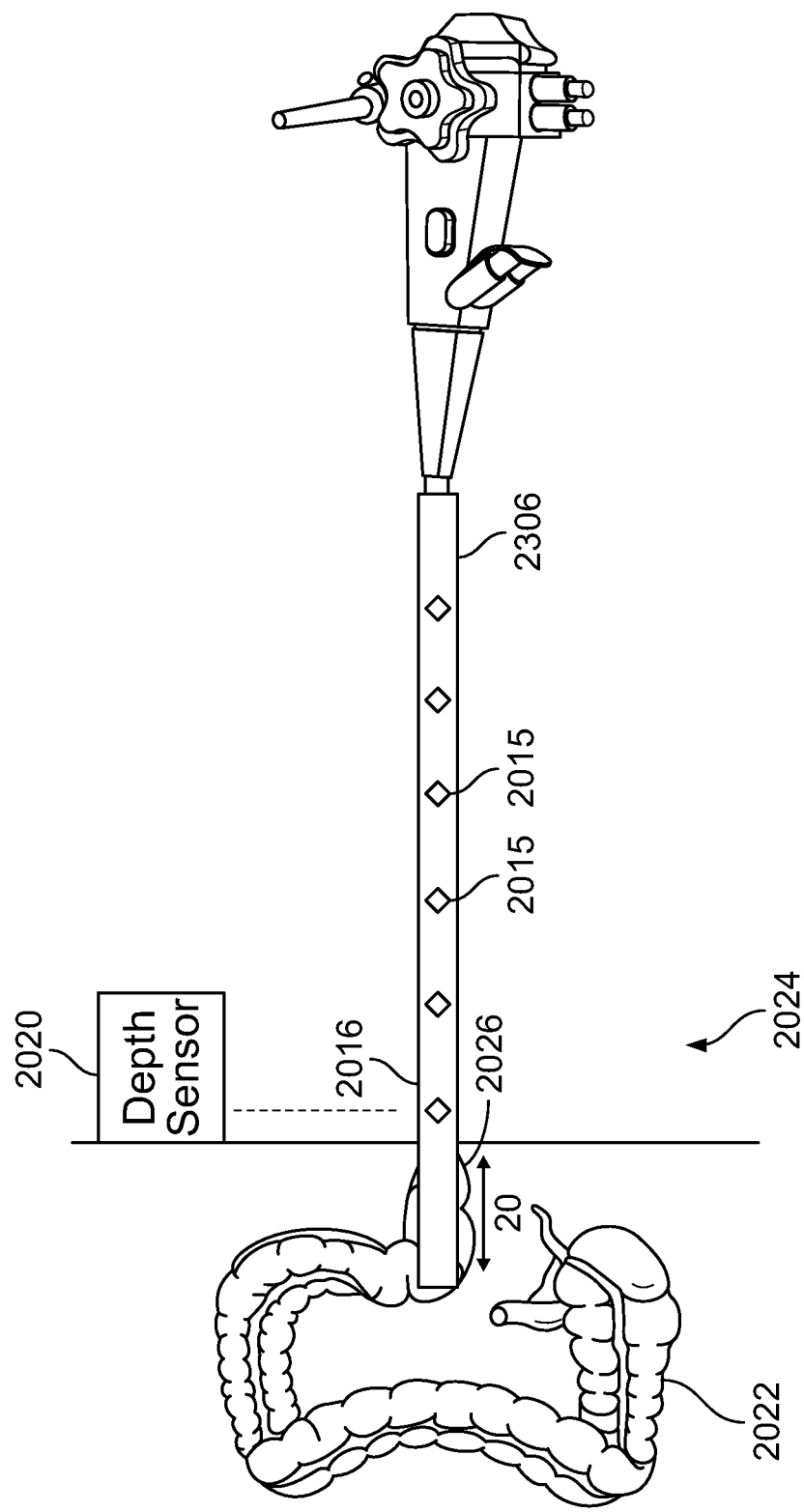
FIG. 2 illustrates a measurement of the depth, distance or location of an endoscopic tip using a multiple viewing elements endoscope whose elongated shaft has a plurality of sensors attached thereto, in accordance with an embodiment of the present specification.

In accordance with another embodiment, the endoscope comprises sensors integrated along its insertion tube to provide real-time information on the distance being travelled by the endoscope inside the patient's lumen. In one embodiment, as shown in FIG. 2, a plurality of sensors 2015 are placed along the elongated shaft or insertion tube 2306 of the endoscope. Further, each sensor has a unique identifier, code, signature, or other identification according to its location (such as distance from the distal tip) along the insertion tube 2306. Thus for example, and not limited to such example, a sensor would be placed at a distance of 1, 2, 3, 4, 5, 6, 7, 8, 9, 10, 11, 12, 13, 14, 15, 16, 17, 18, 19, or 20 centimeters, or any increment therein, from the distal end of the tube 2306. The next sensor may be placed at a similar, or different, distance and would have an identifier that is different than the identifier programmed into the first sensor. In another embodiment, each identifier is not only unique to the sensor but also indicative of the particular position, or distance, occupied by the sensor. Thus, in one embodiment, a plurality of sensors are placed at 10 centimeter increments along the length of the insertion tube 2306 where each sensor 2015 has a different identifier and where each identifier is indicative of the distance increment occupied by the sensor.

Additionally, a depth sensor is placed at the entrance of the body where the endoscope is inserted and is in communication with the main control unit that is used with the endoscope. As a non-limiting example we consider an endoscopic procedure being performed for a patient's colon 2022. The depth sensor 2020 is placed outside the body 2024, close to the rectum 2026, which is the entry point for an endoscope into the colon 2022. In operation, the depth sensor 2020 detects alignment to sensor 2016 closest to the entrance site, outside the body. In one embodiment, each sensor 2015, 2016 is pre-programmed to be read according to its location, such that the 10 cm sensor would transmit a different output than the 20 cm sensor. In one embodiment, the output of the depth sensor 2020 is conveyed to the controller or main control unit, which records and provides a display of the distance travelled by the distal end of the scope.

Figure 3:
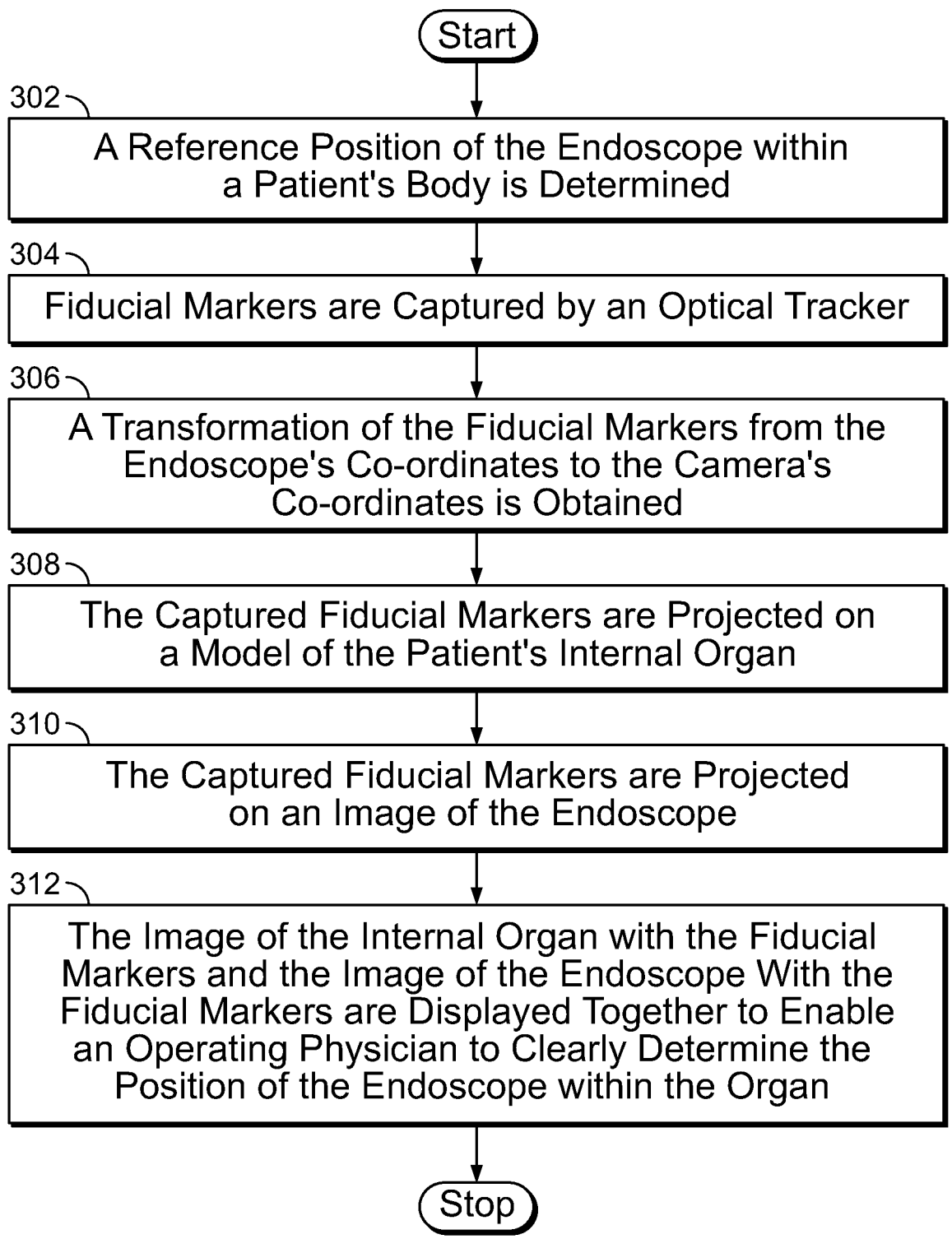
FIG. 3 is a flowchart illustrating a method of tracking a position of an endoscope within a patient's internal organ during an endoscopic procedure, in accordance with an embodiment of the present specification.

FIG. 3 is a flowchart illustrating a first method of tracking the position of an endoscope within a patient's internal organ during an endoscopic procedure, in accordance with an embodiment of the present specification. At step 302, a reference position of the endoscope within a patient's body is determined either in the scope's coordinate system (internal) or an external coordinate system.

In an embodiment, to determine a position of the scope within a patient's body using the scope's coordinate system, fiducial markers are placed on the handle of the endoscope.

In another embodiment, the scope's position within a patient's body may be determined by an external coordinate system, such as by using a bending matrix, electromagnetic tracking, or by using one or more sensors as described above. In such an embodiment, fiducial markers are placed on the external reference coordinate tracking system.

At step 304, fiducial markers, either located on the scope's handle or the external coordinate tracking system, are captured by an optical tracker. In an embodiment, the optical tracker is a camera that captures fiducial markers with respect to the camera's coordinates. In the case where the fiducial markers are rigidly attached to the endoscope, the markers can also be described with respect to the endoscope's coordinates.

Figure 4A:
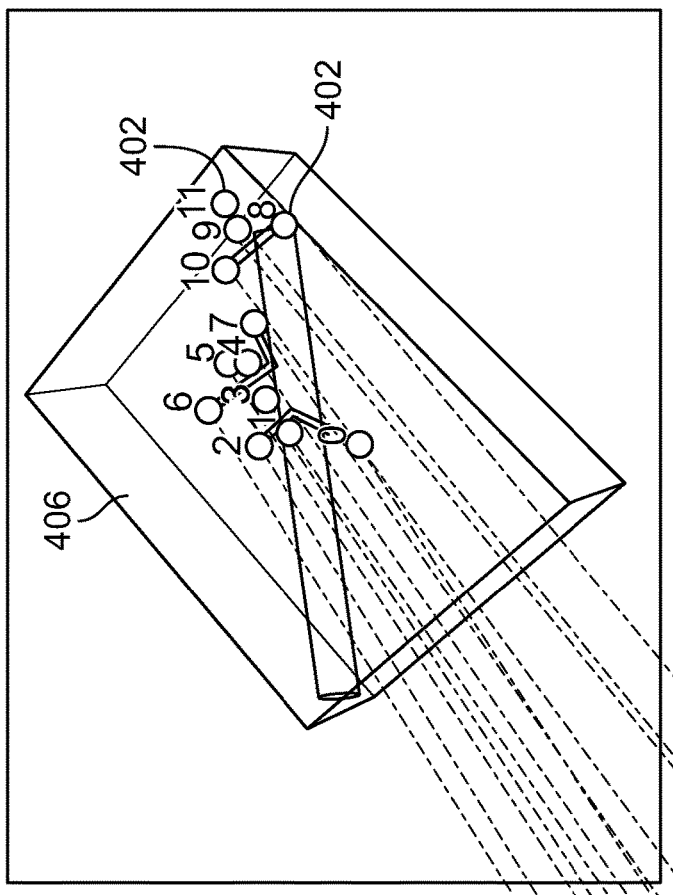
FIG. 4A illustrates a three-dimensional (3D) model of an endoscope with fiducial markers, in accordance with an embodiment of the present specification.
Figure 4C:
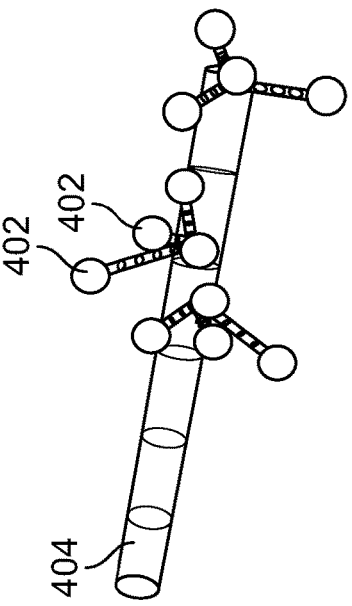
FIG. 4C illustrates the fiducial markers shown in FIG. 4A projected on top of an image of an endoscope captured by the same camera, in accordance with an embodiment of the present specification.
Figure 4B:
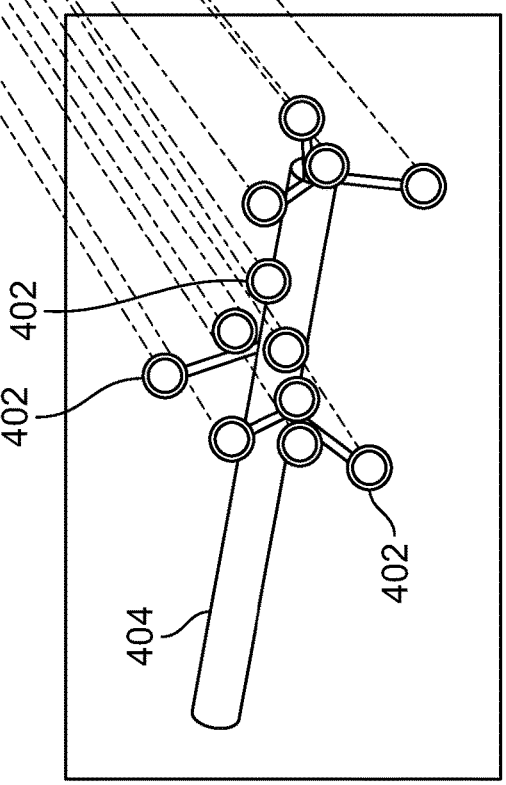
FIG. 4B illustrates the 3D endoscope model shown in FIG. 4A projected onto a two-dimensional (2D) plane by an optical tracker/camera.

FIG. 4A illustrates a three-dimensional (3D) model of a scope with fiducial markers, in accordance with an embodiment of the present specification. FIG. 4B illustrates the 3D scope model shown in FIG. 4A projected onto a two-dimensional (2D) plane by an optical tracker/camera. As shown, fiducial markers 402 are captured in an image by an optical tracker (not shown in the figure) with respect to an endoscope 404. In an embodiment, the optical tracker is a camera that captures fiducial markers 402 with respect to the camera's coordinates. Hence, FIG. 4B illustrates the fiducial markers shown in FIG. 4A matching up to a model of a human colon, in accordance with an embodiment of the present specification. An object detection algorithm is used to detect the captured fiducial markers 402 within the frame/model 406 of the patient's colon. The circles or demarcations (in this case, orange) around the fiducial markers 402 are indications that the fiducial markers 402 are detected (and marked) by a fiducial detection algorithm as explained in step 306 of FIG. 3 below.

At step 306, a transformation of the fiducial markers from the endoscope's coordinates to the optical tracker's coordinates is obtained. The transformation method is dependent on the optical tracker's characteristics. If the optical tracker is composed of two stereo-calibrated cameras, then these cameras compute the 3D location of the fiducials in their own coordinate system by triangulation. However, if the optical tracker is composed of a single camera, then the transformation can be computed by any algorithm that solves the PnP problem, such as EPnP, DLT, and POSSIT.

At step 308, the captured fiducial markers are projected on an image of the patient's internal organ. A 3D image of the internal organ displaying the captured fiducial markers may be obtained by using computer software. At step 310, the captured fiducial markers corresponding to the endoscope are projected on an image of the endoscope. A 3D image of the endoscope displaying the captured fiducial markers may be obtained by using computer software as illustrated in FIG. 4C. FIG. 4C illustrates the fiducial markers shown in FIG. 4A projected on top of the image captured by the same optical tracker/camera, in accordance with an embodiment of the present specification. The fiducial markers 402 shown in FIG. 4A are projected on an image of the endoscope 404, as illustrated. In an embodiment, the accuracy of the position of the camera (not shown in the figure) may be estimated by computation of the camera's re-projection error.

At step 312, the image of the internal organ along with the fiducial markers and the image of the endoscope with the fiducial markers are displayed together to enable an operating physician to clearly determine the position of the endoscope within the organ. In an embodiment, after determining the external camera's parameters (by calibration) a virtual model of the patient's colon showing the position of the endoscope is augmented to the patient image taken by the external camera.

In various embodiments, the patient image may be augmented with the virtual model of the patient's colon showing the position of the endoscope by using a computer monitor display. In other embodiments, display methods such as a see-through glass may be used. In another embodiment, the augmented image may also be displayed on a viewer's retina.

The above examples are merely illustrative of the many applications of the system of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

I claim:

1. An endoscope system having an endoscope, wherein the endoscope includes an endoscope handle and an endoscope body adapted to be inserted into a patient, the system comprising:
    a plurality of orientation markers positioned on the endoscope handle;
    a plurality of first sensors positioned at different locations longitudinally along the endoscope body, wherein each of the plurality of first sensors is adapted to generate first orientation data;
    one or more cameras positioned external to the patient and adapted to detect one or more of the plurality of orientation markers and generate second orientation data;
    a controller adapted to: (i) receive the first orientation data and the second orientation data, and (ii) generate, using the first orientation data and the second orientation data, a virtual model of the endoscope body in a coordinate system of the endoscope and the patient showing a position of the endoscope within the patient; and
    a projector adapted to: (i) receive data indicative of the virtual model from the controller, and (ii) project the virtual model onto the patient to show the position of the endoscope body relative to the patient.

2. The endoscope system of claim 1, wherein the first sensors are pressure sensors.

3. The endoscope system of claim 1, further comprising at least one electromagnetic coil wound around one or more portions of the endoscope body, wherein the electromagnetic coil is configured to emit an electromagnetic signal.

4. The endoscope system of claim 3, further comprising an electromagnetic tracking device external to the endoscope, wherein the electromagnetic tracking device is configured to receive the electromagnetic signal from the electromagnetic coil to track a position of the endoscope.

5. The endoscope system of claim 1, wherein the one or more cameras include two stereo-calibrated cameras adapted to generate, by triangulation, at least a portion of the second orientation data comprising three-dimensional location of fiducials in a coordinate system of the camera.

6. The endoscope system of claim 1, wherein the virtual model is a holographic virtual model.

7. The endoscope system of claim 1, further comprising a plurality of additional sensors including one or more of accelerometers, gyroscopes, magnetometers, and stripes that measure the bending and twisting of an insertion tube of the endoscope by one or more of electro-optic and mechanical methods.

8. An endoscope system having an endoscope, wherein the endoscope includes an endoscope handle and an endoscope body adapted to be inserted into a patient, the system comprising:
  a plurality of orientation markers positioned on the endoscope handle;
  a plurality of pressure sensors positioned at different locations longitudinally along the endoscope body, wherein each of the plurality of pressure sensors is adapted to generate first orientation data and first pressure data;
  one or more cameras positioned external to the patient and adapted to: (i) detect one or more of the plurality of orientation markers and (ii) generate second orientation data;
  a controller adapted to: (i) receive the first orientation data, the first pressure data, and the second orientation data, and (ii) generate, using the first orientation data and the second orientation data, a virtual model of the endoscope body in a coordinate system of the endoscope body and the patient showing a position of the endoscope body within the patient;
  a projector adapted to: (i) receive data indicative of the virtual model from the controller, and (ii) project the virtual model of the endoscope body in a coordinate system of the endoscope body and the patient showing a position of the endoscope body within the patient.

9. The endoscope system of claim 8, wherein the virtual model is a holographic model.

10. The endoscope system of claim 8, wherein the projector is adapted to project the virtual model on the patient, and
  wherein the one or more cameras include two stereo-calibrated cameras adapted to generate, by triangulation, at least a portion of the second orientation data comprising three-dimensional location of fiducials in a coordinate system of the camera.

11. The endoscope system of claim 8, further comprising:
  at least one electromagnetic coil wound around one or more portions of the endoscope body, wherein the electromagnetic coil is configured to emit an electromagnetic signal, and
  an electromagnetic tracking device external to the endoscope, wherein the electromagnetic tracking device is configured to receive the electromagnetic signal from the electromagnetic coil to track a position of the endoscope.

12. The endoscope system of claim 8, further comprising a plurality of additional sensors including one or more of accelerometers, gyroscopes, magnetometers, and stripes that measure the bending and twisting of an insertion tube of the endoscope by one or more of electro-optic and mechanical methods.

13. An endoscope system having an endoscope, wherein the endoscope includes an endoscope handle and an endoscope body adapted to be inserted into a patient, the system comprising:
  a plurality of orientation markers positioned on the endoscope handle;
  a plurality of first sensors positioned at different locations longitudinally along the endoscope body, wherein each of the plurality of first sensors is adapted to generate first orientation data;
  one or more cameras positioned external to the patient and adapted to: (i) detect one or more of the plurality of orientation markers and (ii) generate second orientation data;
  a controller adapted to: (i) receive the first orientation data and the second orientation data, and (ii) generate, using the first orientation data and the second orientation data, a virtual model of a position of the endoscope body in a coordinate system of the endoscope body and the patient showing a position of the endoscope body within the patient; and
  a projector adapted to: (i) receive data indicative of the virtual model from the controller, and (ii) project the virtual model of the endoscope body in a coordinate system of the endoscope body and the patient showing a position of the endoscope body within the patient.

14. The endoscope system of claim 13, further comprising a plurality of additional sensors including one or more of accelerometers, gyroscopes, magnetometers, and stripes that measure the bending and twisting of an insertion tube of the endoscope by one or more of electro-optic and mechanical methods.

15. The endoscope system of claim 13, further comprising:
  at least one electromagnetic coil wound around one or more portions of the endoscope body, wherein the electromagnetic coil is configured to emit an electromagnetic signal; and
  an electromagnetic tracking device external to the endoscope, wherein the electromagnetic tracking device is configured to receive the electromagnetic signal from the electromagnetic coil to track a position of the endoscope.

16. The endoscope system of claim 13, wherein the projector is adapted to project the virtual model on the patient.

17. The endoscope system of claim 13, wherein the virtual model is a holographic model.

18. The endoscope system of claim 13, wherein the controller is adapted to generate an image of the patient positioned on the patient bed.

19. The endoscope system of claim 13, wherein the virtual model includes a portion of the patient's colon.

20. The endoscope system of claim 13, further comprising at least one orientation marker positioned on a patient bed.

* * * * *